United States Patent
Lai

(10) Patent No.: US 6,649,591 B2
(45) Date of Patent: Nov. 18, 2003

(54) POLYDITHICARBAMATE-CONTAINING NON-TARGETING MARCOMOLECULES AND THE USE THEREOF FOR THERAPEUTIC AND DIAGNOSTIC APPLICATIONS

(75) Inventor: Ching-San Lai, Encinitas, CA (US)

(73) Assignee: Medinox, Inc., San Diego, CA (US)

( * ) Notice: Subject to any disclaimer, the term of this patent is extended or adjusted under 35 U.S.C. 154(b) by 43 days.

(21) Appl. No.: 09/409,645

(22) Filed: Oct. 1, 1999

(65) Prior Publication Data

US 2002/0045573 A1 Apr. 18, 2002

Related U.S. Application Data

(63) Continuation-in-part of application No. 08/899,087, filed on Jul. 23, 1997, now abandoned.
(60) Provisional application No. 60/025,867, filed on Sep. 10, 1996, now abandoned.

(51) Int. Cl.$^7$ .......................... A61K 38/16; C07K 14/00
(52) U.S. Cl. .......................... 514/6; 424/9.3; 424/9.34; 424/9.35; 514/2; 514/44; 514/54; 514/476; 514/483; 530/403; 530/404; 530/405; 536/22.1; 536/123; 536/123.1
(58) Field of Search .......................... 514/2, 6, 44, 54, 514/476, 483; 530/403, 404, 405; 536/22.1, 123, 123.1; 424/9.3, 9.34, 9.35

(56) References Cited

U.S. PATENT DOCUMENTS

| | | | |
|---|---|---|---|
| 4,046,722 A | * | 9/1977 | Rowland |
| 4,160,452 A | | 7/1979 | Theeuwes ............... 128/260 |
| 4,256,108 A | | 3/1981 | Theeuwes ............... 128/260 |
| 4,265,874 A | | 5/1981 | Bonsen et al. .............. 424/15 |
| 4,385,046 A | * | 5/1983 | Milbrath et al. |
| 5,057,313 A | * | 10/1991 | Shih et al. |
| 5,387,748 A | | 2/1995 | Demuth, Jr. et al. ........ 514/254 |
| 5,559,214 A | * | 9/1996 | Delecki et al. |
| 5,730,968 A | * | 3/1998 | Butterfield et al. ...... 424/78.37 |
| 5,783,596 A | * | 7/1998 | Medford et al. ............ 514/423 |
| 5,869,348 A | * | 2/1999 | Lai ............................ 436/543 |

FOREIGN PATENT DOCUMENTS

WO    WO 98/11066    *    3/1998

OTHER PUBLICATIONS

Mashiba et al, Int. Jour. Immunother., VI, 221–224, 1990.*
Mashiba et al, Cancer Letters, 55, 183–188, 1990.*
Guclu et al., "Binding of Chlorambucil with Antitumor Globulins and its Effect on Drug and Antibody Activities" *Europ. J. Cancer*, vol. 12:95–100 (1976).
Martens et al., "Ditiocarb: Decomposition in Aqueous Solution and Effect of the Volatile Product on Its Pharmacological Use" *Journal of Pharmaceutical Sciences* vol. 82:379–383 (1993).

Aptaker et al., "Serum Albumin Level as a Predictor of Geriatric Stroke Rehabilitation Outcome" *Arch. Phys. Med. Rehabil.*, 75:80–84 (1994).
Avontuur et al., "Inhibition of Nitric Oxide Synthesis Causes Myocardial Ischemia in Endotoxemic Rats" *Cir. Res.*, 76:418–425 (1995).
Beckman et al., "Apparent hydroxyl radical production by peroxynitrite: Implications for endothelial injury from nitric oxide and superoxide" *Proc.Natl. Acad. Sci.*, USA 87:1620–1624 (1990).
Bredt and Snyder, "Nitric Oxide: A Physiologic Messenger Molecule" *Neuron*, 8:3–11.
Caldwell et al., "$N^G$–Nitro–L–arginine methyl ester protects lipid peroxidation in the gerbil following cerebral ischaemia" *Eur. J. Pharmacol.*, 285:203–206 (1995).
Chan, "Role of Oxidants in Ischemic Brain Damage" *Stroke*, 27:1127–29 (1996).
Dawson and Dawson, "Protection of the Brain from Ischemia" *Cerebrovascular Disease*, H. Hunt Batjer, ed., Lippincott–Raven Publishers, Philadelphia, Ch. 25 pp. 319–325 (1997).
Diener et al., "Lubeluzole in Acute Ischemic Stroke: A Double–blind, Placebo–Controlled Phase II Trial" *Stroke*, 27:76–81 (1996).
Diket et al., "Nitric oxide inhibition causes intruterine growth retardation and hind–limb disruptions in rats" *Am. J. Obstet. Gynecol.*, 171:1243–1250 (1994).

(List continued on next page.)

Primary Examiner—David Saunders
(74) Attorney, Agent, or Firm—Stephen E. Reiter; Foley & Lardner

(57) ABSTRACT

In accordance with the present invention, there is provided a new class of drugs for therapeutic treatment of such indications as cerebral stroke and other ischemia/reperfusion injury. Thus, in accordance with the present invention, dithiocarbamates are linked to the surface of a non-immunogenic, non-targeting macromolecule other than an antibody (e.g., albumin protein) either by using cross-linking reagents or by nonspecific binding to produce polydithiocarbamate-macromolecule-containing compositions, which represent a new class of drugs for therapeutic treatment of such indications as cerebral stroke and other ischemia/reperfusion injury. In accordance with another aspect of the present invention, combinational therapeutic methods have been developed for the in vivo inactivation or inhibition of formation (either directly or indirectly) of species which induce the expression of inducible nitric oxide synthase, as well as reducing nitric oxide levels produced as a result of .NO synthase expression. In accordance with yet another aspect of the present invention, magnetic resonance imaging methods have been developed for the measurement of cerebral and cardiac blood flow and infarct volume in ischemic stroke or heart attack situations. Such methods employ iron-containing complexes of a composition comprising a dithiocarbamate and a non-immunogenic, non-targeting macromolecule other than an antibody as contrast agents.

18 Claims, 1 Drawing Sheet

OTHER PUBLICATIONS

Dizdaroglu and Bergtold, "Characterization of Free Radical–Induced Base Damage in DNA at Biologically Relevant Levels" *Anal. Biochem.*, 156:182–188 (1986).

Faraci and Brian, "Nitric Oxide and the Cerebral Circulation" *Stroke*, 25:692–703 (1994).

Fisher et al., "New Magnetic Resonance Techniques for Evaluating Cerebrovascular Disease" *Ann. Neurol.*, 32:115–122 (1992).

Haber and Weiss, "The Catalytic Decomposition of Hydrogen Peroxide by Iron Salts*" *Proc. R. Soc. Ser. A.*, 147:332–351 (1934).

Haley, "Safety Study of Tirilazad Mesylate in Patients With Acute Ischemic Stroke (STIPAS)" *Stroke*, 25:418–423 (1994).

Halliwell, "Albumin—An Important Extracellular Antioxidant?" *Biochem. Pharmacol.*, 37:569–571 (1988).

Hassan et al., "Biosynthesis and Regulation of Superoxide Dismutases" *Free Radical Biol. Med.*, 5:377–385, (1988).

He et al., "Polyethylene glycol–conjugated superoxide dismutase in focal cerebral ischemia–reperfusion" *Am. J. Physiol.* 265:H252–256 (1993).

Hearse et al., "The Oxygen Paradox and the Calcium Paradox: Two Facets of the Same Problem?" *J. Mol. Cell. Cardiol.*, 10:641–668 (1978).

Huie and Padmaja, "The Reaction of no with Superoxide" *Free Radical Res. Commun.*, 18:195–199 (1993).

Iadecola et al., "Inducible Nitric Oxide Synthase Gene Expression in Brain Following Cerebral Ischemia" *J. Cereb. Blood Flow and Metab.*, 15:378–384 (1995).

Komarov and Lai, "Detection of nitric oxide production in mice by spin–rapping electron paramagnetic resonance spectroscopy" *Biochim. Biophys. Acta*, 1272:29–36 (1995).

Kumura et al., "Elevation of Plasma Nitric Oxide End Products During Focal Cerebral Ischemia and Reperfusion in the Rat" *J. Cereb. Blood Flow and Metab.*, 14:487–491 (1994).

Lai and Komarov, "Spin trapping of nitric oxide produced in vivo in setic–shock mice" *FEBS Letters*, 345:120–124 (1994).

Lai and Piette, "Hydroxyl Radical Production Involved in Pipid Peroxidation of Rat Liver Microsomes*" *Biochem. Biophys. Res. Comun.*, 78:51–59 (1977).

Lenzi et al., "Early Treatment of Strok With Monosialoganglioside GM–1" *Stroke*, 5:1552–1558 (1994).

Lin et al., "Effect of Brain Edema on Infarct Volume in a Focal Cerebral Ischemia Model in Rats" *Stroke* 24:117–121 (1993).

Malinski et al., "Nitric Oxide–Induced Blockade of NMDA Receptors" *J Cereb.Blood Flow Metab.*, 13:355–358 (1993).

Manzoni et al., "Nitric Oxide Measured by Porphyrinic Microsensor in Rat Brain After Transient Middle Cerebral Artery Occlusion" *Neuron*, 8:653–662 (1992).

Matsui et al., "Beneficial Effect of Prolonged Administration of Albumin on Ischemic Cerebral Edema and Infarction after Occlusion of Middle Cerebral Artery in Rats" *Neurosurgery*, 33:293–300 (1993).

Meldrum, "Cytoprotective therapies in stroke" *Current Opinion in Neurol.*, 8:15–23 (1995).

Moncada and Higgs, "The L–Arginine—Nitric Oxide Pathway" *New Engl. J. Med.*, 329:2002–2012 (1993).

Nathan, "Nitric oxide as a secretory prodcut of mammalian cells" *FASEB J.*, 6:3051–3064 (1992).

Reisinger et al., "Inhibition of HIV progression by dithiocarb" *Lancet*, 335:679–82 (1990).

Samdani et al., "Nitric Oxide Synthase in Models of Focal Ischemia" *Stroke* 28:1283–1288 (1997).

Sato et al.. "EPR spin–trapping study of nitric oxide formation during bilateral carotid occlusion in the rat" *Biochim. Biophys. Acta*, 1181:195–197 (1993).

Sunderman, "Efficacy of Sodium Diethyldithiocarbamate (Dithiocarb) in Acute Nickel Carbonyl Poisoning*" *Annals Clin. Res.*, 3:182–185 (1971).

Warach et al., "Fast magnetic resonance diffusion–weighted imaging of acute human stroke" *Neurol.*, 42:1717–1723 (1992).

Wityk and Stern, "Ischemic stroke: Today and tomorrow" *Crit. Care Med.*, 22:1278–1293.

Zhang et al., "Aminoguanidine Ameliorates and L–Arginine Worsens Brain Damage From Intraluminal Middle Cerebral Artery Occlusion" *Stroke*, 27:317–323 (1996).

* cited by examiner

POLYDITHICARBAMATE-CONTAINING NON-TARGETING MARCOMOLECULES AND THE USE THEREOF FOR THERAPEUTIC AND DIAGNOSTIC APPLICATIONS

RELATED APPLICATIONS

This application is a continuation-in-part of U.S. patent application Ser. No. 08/899,087, filed Jul. 23, 1997, now abandoned, which relies for priority upon U.S. Provisional Application Ser. No. 60/025,867, filed Sep. 10, 1996, now abandoned, the entire contents of each of which are hereby incorporated by reference herein.

FIELD OF THE INVENTION

The present invention relates to novel non-targeting dithiocarbamate-containing compositions. In one aspect, the present invention relates to non-targeting dithiocarbamate-containing compositions wherein the dithiocarbamate is non-covalently associated with a macromolecule other than an antibody. Preferably, the macromolecule is non-immunogenic. In another aspect, the present invention relates to non-targeting dithiocarbamate-containing compositions wherein the dithiocarbamate is covalently crosslinked with a macromolecule other than an antibody that is preferably non-immunogenic. In yet another aspect, the present invention relates to diagnostic and therapeutic methods employing the novel non-targeting dithiocarbamate-containing compositions described herein.

BACKGROUND OF THE INVENTION

In 1984, Jolly et al., demonstrated the protection of reperfused myocardial tissue with the combinational use of superoxide dismutase and catalase (see, for example, Jolly et al., Cir. Res., 57:277, 1984). This observation implied that oxygen-derived free radicals are a cause of the reperfusion injury to the hypoxic myocardium. It is now known, however, that the phenomenon of ischemia/reperfusion injury is not restricted to the myocardium. Instead, ischemia/reperfusion injury is viewed as a general damaging event in any tissue or organ (such as brain, liver or kidney) subjected to a critical period of ischemia followed by perfusion with oxygenated whole blood.

Ischemia/reperfusion injury therefore results from the reintroduction of molecular oxygen at the time of organ reperfusion or restoration of the circulation. While the delivery of dissolved molecular oxygen sustains cellular viability, it also provides oxygen as a substrate for numerous enzymatic oxidation reactions that produce reactive oxygen species which cause oxidative damage, a phenomenon referred to as the "oxygen paradox" (see, for example, Hearse et al., in J. Mol. Cell. Cardiol., 10:641, 1978). Oxygen, a gaseous molecule essential for normal cellular metabolism, can, under certain conditions, be deleterious to life. The cell defends itself against oxidative insults through its antioxidant mechanisms including superoxide dismutase (SOD), catalase, glutathione peroxidase, glutathione reductase and cellular antioxidants including glutathione, ascorbate and a-tocopherol (see, for example, Chan, in Stroke, 27:1124–29, 1996). However, when reactive oxygen species are generated at a rate that exceeds the capacity of the cell to defend itself against the resulting oxidative stress (such as in ischemia/reperfusion insults), the cell is irreversibly damaged, resulting in necrotic cell death or ischemic cell death.

Although the exact mechanism by which oxygen induces ischemic cell death is not yet clear, it is well known that reactive oxygen species cause a wide range of tissue damage. The hydroxyl radical (.OH), the most potent oxidant, is capable of initiating lipid peroxidation, causing protein oxidation and DNA damage in cells (see, for example, Lai and Piette, in Biochem. Biophys. Res. Commun., 78:51–59, 1977 and Dizdaroglu and Bergtold, in Anal. Biochem., 156:182, 1986). Albeit less reactive, superoxide anion radicals ($.O_2^-$), on the other hand, participate in a repertoire of oxidative reactions which generate hydrogen peroxide and hydroxyl radical as follows:

$$.O_2^- + .O_2^- \rightarrow H_2O_2 \qquad (1)$$

$$.O_2^- + H_2O_2 \rightarrow .OH + OH^- + O_2 \qquad (1)$$

Reaction (1) is catalyzed by SOD, while reaction (2) proceeds rapidly in the presence of trace iron metal (see, for example, Haber and Weiss, in Proc. R. Soc. Ser. A., 147:332, 1934). Superoxide anion radical is known to liberate iron from ferritin (see, for example, Wityk and Stem, in Crit. Care Med., 22:1278–93, 1994) which further facilitates the iron-catalyzed Fenton reaction in the reoxygenated tissue, generating damaging hydroxyl radicals, as shown in reactions (3) and (4), see, for example, Halliwell and Gutteridge, in Halliwell and Gutteridge. Free Radicals in Biology and Medicine, 2nd edition. Oxford: Clarendon Press, 15–19 (1989):

$$Fe^{3+} + O_2^- \rightarrow Fe^{2+} + O_2 \qquad (3)$$

$$Fe^{2+} + H_2O_2 \rightarrow .OH + OH^- + Fe^{3+} \qquad (4)$$

In addition to reactive oxygen species, reactive nitrogen species such as nitric oxide (.NO) have also been observed to be excessively produced in ischemia/reperfusion organs (see, for example, Faraci and Brian, in Stroke, 25: 692–703, 1994). .NO is synthesized from the terminal guanidino nitrogen atom of L-arginine by nitric oxide synthase (NOS). Three different isoforms of NOS have been isolated, cloned, sequenced and expressed (see, for example, Nathan, in FASEB J., 6:3051–3064, 1992), i.e., eNOS, NNOS and iNOS. The eNOS (endothelial cell derived) and nNOS (neuronal cell derived) are expressed constitutively, and both enzymes require an increase in intracellular calcium for activation.

Under physiological conditions, a low output of .NO is released continuously from eNOS in endothelial cells and from nNOS in neuronal cells. This .NO serves to dilate blood vessels and, in concert with vasoconstrictor catecholamines, regulate blood flow and blood pressure. On the other hand, a high output of .NO is produced by the inducible, calcium-independent NOS (INOS) isoform upon activation with cytokines or endotoxin (see, for example, Moncada and Higgs, in New Engl. J. Med., 329:2002–2012, 1993). iNOS is expressed in numerous cell types, including endothelial cells, smooth muscle cells, microglial cells and macrophages. Abnormally elevated levels of nitric oxide have recently been associated with ischemia/reperfusion injury (see, for example, Kumura et al., in J. Cereb. Blood Flow and Metab., 14:487–491, 1994; Iadecola et al., J. Cereb. Blood Flow and Metab., 15:378–384, 1995).

In the central nervous system, nitric oxide has been discovered to function as both a neurotransmitter and a neurotoxin (see, for example, Faraci and Brian, in supra.). It mediates N-methyl-D-aspartate (NMDA) excitotoxicity. Elevated .NO levels in the brain have been measured during ischemia using an .NO electrode (for example, see Malinski et al., J Cereb.Blood Flow Metab., 13:355–358,1993), and by electron paramagnetic resonance spin trapping (for example, Sato et al., Biochim. Biophys. Acta, 1181:195–197, 1993). .NO levels began to increase within minutes after the onset of ischemia, presumably reflecting an increased activity of constitutive .NO synthase. However, as ischemia continues, .NO levels fall slowly but then increase again during reperfusion (see, for example, the recent review by Dawson and Dawson in Cerebrovascular Disease, H. Hunt Batjer, ed., Lippincott-Raven Publishers, Philadelphia, pp. 319–325 (1997)). The expression of iNOS gene was demonstrated in the rat brain to begin at 12 hours and peaked at 48 hours following the cerebral ischemia (Iadecola et al., supra).

.NO may have both beneficial and detrimental effects during cerebral ischemia. Increased .NO production during ischemia may be protective because .NO increases cerebral blood flow and inhibition of aggregation and adherence of platelets or leukocytes (see, for example, Samdani et al., in Stroke 28:1283–1288 (1997)). On the other hand, excessive .NO production during reperfusion is cytotoxic, either directly or after recombination with superoxide anion radical to form peroxynitrite according to reactions (5)–(7), as follows:

$$.O_2^- + .NO \rightarrow ONOO^- \quad (5)$$

$$ONOO^- + H^+ \rightarrow ONOOH \quad (6)$$

$$ONOOH \rightarrow [.OH] + .NO_2 \quad (7)$$

It has been demonstrated in cell-free systems that superoxide anion radical chemically reacts with nitric oxide to form the toxic anion, peroxynitrite, $ONOO^-$ (reaction (5), see, for example, Beckman et al., in Proc.Natl. Acad. Sci., USA 87:1620–1624, 1990). The rate constant for the reaction of nitric oxide with superoxide anion is $6.7 \times 10^9 \, M^{-1}S^{-1}$ (see, for example, Huie and Padmaja, in Free Radical Res. Commun., 18:195–199, 1993) which is three times faster than that for the dismutation of superoxide anion radicals by superoxide dismutase (reaction (1); $2-3 \times 10^9 \, M^{-1}S^{-1}$) (see, for example, Hassan et al., in Free Radical Biol. Med., 5:377–385, 1988). At physiological pH, peroxynitrite is essentially protonated (reaction (6)), which decomposes readily to form a hydroxyl radical-like species (i.e., "[.OH]"), a potent cytotoxic molecule to cells (reaction (7)).

Thus, it is possible that the eventual pathway leading to ischemia/reperfusion injury may arise from hydroxyl radicals or hydroxy radical-like species produced by peroxynitrite as a result of simultaneously increased superoxide anion and nitric oxide. Studies using cultured neurons suggest that both NMDA- and glutamate-induced neurotoxicity and neuronal damage due to hypoxia may be mediated by .NO (see, for example, Bredt and Snyder, Neuron, 8: 3–11, 1992 and Manzoni et al., Neuron, 8:653–662,1992).

Several drugs, aimed at blocking free radical-induced reperfusion injury, have been developed and tested in animals and humans. They can be categorized into two major types, namely, inhibitors and scavengers. For example, ganglioside GM-1 (which binds calmodulin and inhibits NOS activities) has been evaluated in acute ischemic stroke (see, for example, Lenzi et al., in Stroke, 5:1552–1558, 1994). However, treatment with GM-1 did not appear to alter patient survival. As another example, lubeluzole, a newly synthesized benzothiazole compound, is in phase II clinical trials for the treatment of acute ischemic stroke (see, for example, Diener et al., in Stroke, 27:7681, 1996). This drug inhibits glutamate-induced nitric oxide-related neurotoxicity by interfering with key mechanisms in the biochemical cascade that lead to ischemic tissue damage.

Clinical trials are also in progress for several other glutamate antagonist drugs, but data have not yet been published (see, for example, Meldrum, in Current Opinion in Neurol., 8:15–23, 1995).

Currently, many pharmaceutical companies have turned their attention to the design and development of substrate or product analogue inhibitors of the nitric oxide synthase enzyme, NOS, in efforts to treat the overproduction of .NO in stroke and other ischemic/reperfusion conditions. For example, aminoguanidine, an NOS inhibitor, was shown to ameliorate the brain damage in cerebral ischemia (see, for example, Zhang et al., in Stroke, 27:317–323, 1996). Inhibition of NOS by $N^G$-nitro-L-arginine decreased lipid peroxidation in the gerbil cerebral ischemia (see, for example, Caldwell et al., in Eur. J. Pharmacol., 285:203–206, 1995).

However, recent data show that the inhibition of NOS is detrimental to subjects. For example, rodent studies have shown that inhibition of the production of .NO causes intrauterine growth retardation and hind-limb disruptions in rats (see, for example, Diket et al., in Am. J. Obstet. Gynecol., 171: 1243–1250, 1994). Furthermore, the inhibition of NOS was found to cause myocardial ischemia in endotoxic rats (see, for example, Avontuur et al., Cir. Res., 76:418–425, 1995).

In contrast to the inhibitory approach described in the prior art to address the problem of free radical overproduction, the free radical scavenging approach also has been taken to reduce excessive reactive oxygen and nitrogen species in vivo. For example, tirilazad mesylate, a free radical scavenger, has been employed in clinical trials for the treatment of stroke patients (see, for example, Haley, in Stroke, 25:418–423 (1994)).

There is, however, still a need in the art for agents which effectively block free radical-induced reperfusion injury, without causing undesirable side effects.

BRIEF DESCRIPTION OF THE INVENTION

In accordance with the present invention, there is provided a new class of drugs for therapeutic treatment of cerebral stroke and other ischemia/reperfusion injury. Thus, in accordance with the present invention, dithiocarbamates are linked to the surface of a macromolecule other than an antibody (e.g., albumin protein) under crosslinking conditions selected to preserve the dithiocarbamate either by using cross-linking reagents or by nonspecific binding to produce non-targeting polydithiocarbamate-macromolecule-containing derivatives and compositions containing such derivatives. The invention derivatives represent a new class of drugs for therapeutic treatment of cerebral stroke and other ischemia/reperfusion injury. There are numerous advantages of the invention polydithiocarbamate-macromolecule-containing compositions for ischemia/reperfusion therapy, including:

(i) providing multiple thiol groups, which are reducing equivalents that are known to react effectively with reactive oxygen species such as superoxide anion and hydroxyl radicals and with reactive nitrogen species such as nitric oxide to form S-nitrosothiol derivatives, (ii) chelating and removing adventitious iron ions released from injured tissues to prevent oxidative damage (caused, for example, by iron-catalyzed oxygen radical reactions), and (iii) forming, upon chelation with iron, a two-to-one [(dithiocarbamate)$_2$-Fe] complex on the surface of the macromolecule. This complex further scavenges excess nitric oxide produced in inflamed tissues such as cerebral infarcts in ischemic stroke.

The simultaneous removal of reactive nitrogen species (such as nitric oxide) and reactive oxygen species (such as superoxide anion radical and hydroxyl radicals) should impede the pathway leading to the formation of peroxynitrite, reducing the generation of reactive hydroxyl radical-like species, as shown in reactions (5)–(7) above, and thus ameliorating ischemia/reperfusion injury.

In accordance with another aspect of the present invention, combinational therapeutic methods have been developed for the in vivo inactivation or inhibition of formation (either directly or indirectly) of species which induce the expression of inducible nitric oxide synthase, as well as reducing nitric oxide levels produced as a result of .NO synthase expression. Invention combinational therapeutic methods can be employed, for example, for the treatment of infectious and/or inflammatory conditions. Thus, the effectiveness of many therapeutic agents used for the treatment of infectious and/or inflammatory conditions can be enhanced by co-administration thereof in combination with the dithiocarbamate-containing nitric oxide scavenger(s) described herein.

Additionally, proton magnetic resonance imaging (MRI) techniques provide important information on images of regions of acute infarctions in cerebral ischemia in humans (see, for example, Warach et al., in Neurol., 42:1717–23, 1992). MRI techniques coupled with the use of contrast agents are being developed to assess cerebral perfusion after ischemic insults (see, for example, Fisher et al., in Ann. Neurol., 32:115–122, 1992). Because of its inherent paramagnetic properties, iron containing complexes of polydithiocarbamate-macromolecule-containing compositions according to the present invention should also be useful as a contrast enhancement agent for the measurement of blood perfusion in various organs including brain, heart, kidney and other vital organs and to assess the infarct area and volume in ischemic stroke and heart attack.

Thus, in accordance with another aspect of the present invention, magnetic resonance imaging methods have been developed for the measurement of cerebral and cardiac blood flow and infarct volume in ischemic stroke or heart attack situations. Such methods employ iron-containing complexes of a composition comprising a dithiocarbamate and a macromolecule as contrast agents. It has been found that conjugation of a dithiocarbamate and a macromolecule, as described herein, produces dithiocarbamate-macromolecule-containing compositions having both free radical scavenging and hemodilution beneficial effects in the treatment of ischemia/reperfusion injury.

DETAILED DESCRIPTION OF THE INVENTION

Figure 1:
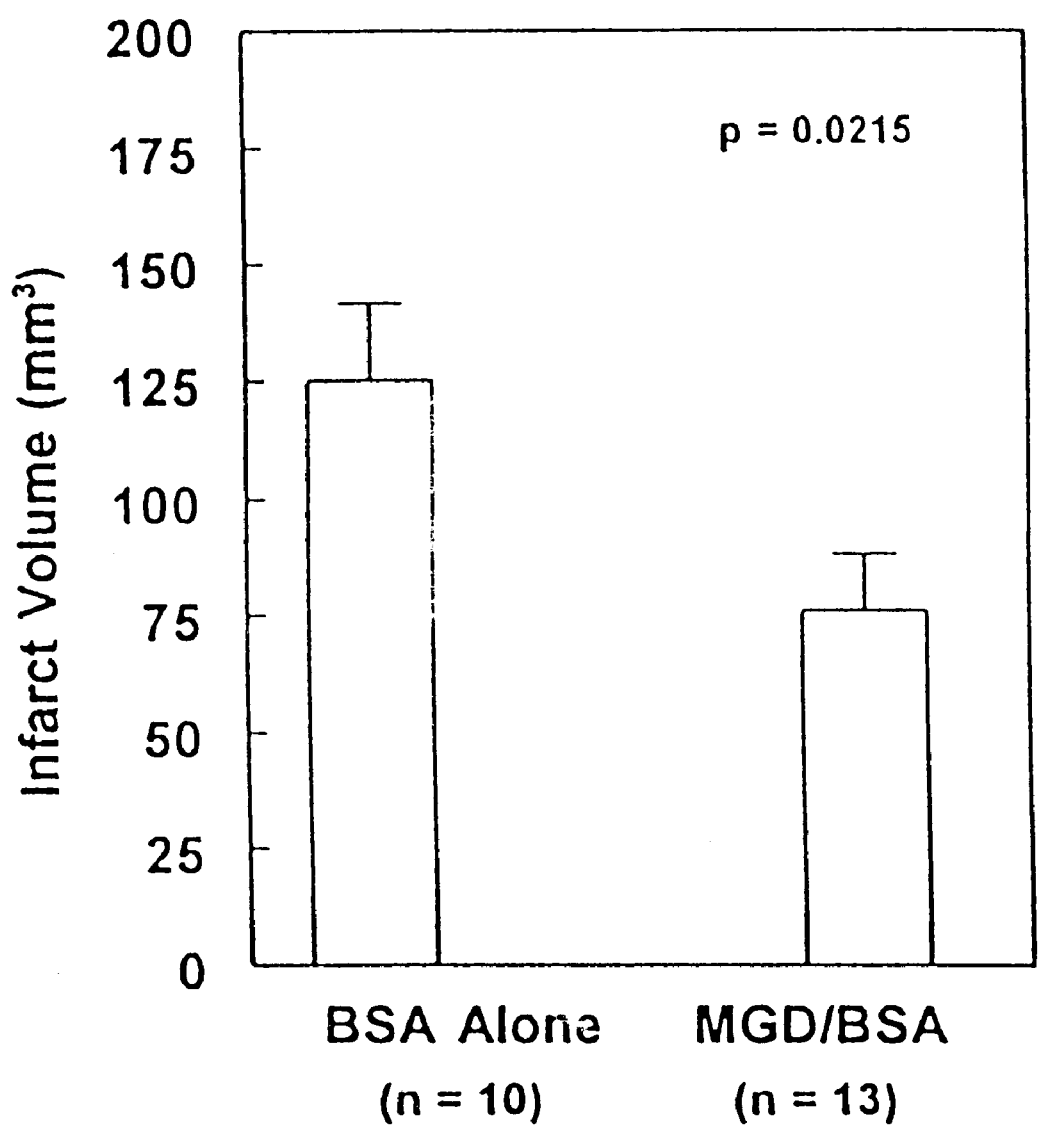
FIG. 1 illustrates the effect on infarct volume when ischemic stroke rats are treated with bovine serum albumin (BSA) in saline or with a combination of BSA with N-methyl-D-glucamine dithiocarbamate (MGD) according to the invention.

In accordance with the present invention, there are provided non-targeting therapeutic compositions comprising a dithiocarbamate non-covalently associated with a macromolecule other than an antibody. Such derivatives are capable of forming a complex with iron, which can further complex with nitric oxide. Thus, there are provided therapeutic derivatives of free dithiocarbamate, as well as therapeutic derivatives of the iron-dithiocarbamate complex, [(dithiocarbamate)$_2$Fe].

In accordance with another aspect of the present invention, there are provided non-targeting therapeutic derivatives comprising at least one dithiocarbamate covalently crosslinked with a macromolecule other than an antibody. Such compositions are also capable of forming a complex with iron, which can further complex with nitric oxide. Thus, there are provided additional therapeutic derivatives of free dithiocarbamate, as well as therapeutic derivatives of the iron-dithiocarbamate complex, [(dithiocarbamate)$_2$Fe].

In accordance with still another aspect of the present invention, there are provided methods for producing the above-described non-targeting therapeutic derivatives of dithiocarbamates. Invention methods comprise contacting a dithiocarbamate with a macromolecule other than an antibody in the presence of a crosslinking agent under crosslinking conditions selected to preserve the dithiocarbamate linkage, for example at a pH in the range from about 6.0 to about 9.0.

In accordance with yet another aspect of the present invention, there are provided combinational therapeutic methods for treating a variety of conditions related to the overproduction of nitric oxide by a subject. In one embodiment, the invention combinational therapeutic method comprises directly or indirectly treating the production of species which induce the expression of inducible nitric oxide synthase in a subject. Invention methods comprise:

co-administering to a subject an effective amount of a combination of at least one agent capable of directly or indirectly inactivating said species, or inhibiting production of said species, and at least one dithiocarbamate-containing nitric oxide scavenger as described herein.

In accordance with another embodiment of the present invention, combinational therapeutic methods have been developed employing an effective amount of a combination of at least one treating agent useful for the treatment of infectious and/or inflammatory conditions, and at least one dithiocarbamate-containing nitric oxide scavenger as described herein. It has been found that the above-described combination is more effective for the treatment of infectious and/or inflammatory conditions than is the treating agent alone.

As used herein, the term "non-targeting derivative" means that the dithiocarbamate derivative does not target to a specific receptor or antigenic site in the cells of body tissue. In other words, the invention derivative does not act like an antibody or other type of ligand that seeks out and binds to a specific bodily or tissue site that is defined by the particular amino acid composition or nucleotide composition of any part of the derivative, especially of the macromolecule contained in the derivative, which is defined herein as being "other than an antibody."

As used herein, the term "non-immunogenic" means that the macromolecule can be administered to a mammal, such as a human, without raising a substantial Type 1 or Type 2 immune response.

Any dithiocarbamate can be employed in accordance with the present invention. Dithiocarbarnates are a class of low molecular-weight sulphur-containing compounds that are effective antioxidants and chelators. For example, diethyldithiocarbamate (DDC) is used clinically for the treatment of nickel poisoning (see, for example, Sunderman, in Annals Clin. Res., 3:182–185, 1971). DDC has also been used in the treatment of cancer, and in human immunodeficiency virus (HIV)-infected patients (see, for example, Reisinger et al., in Lancet, 335:679–82, 1990). Recent studies have shown that DDC acts either as a direct scavenger of hydroxyl radicals (due to its thiol groups) or as an iron-chelator that inhibits hydroxyl radical production by binding iron ions, or by both mechanisms (see, for example, Liu et al., in Free Rad. Res., 24:461–472, 1996). Additionally, it has recently been found that N-methyl-D-glucamine dithiocarbamate (MGD) chelates with ferrous iron as a two-to-one [(MGD)$_2$/Fe] complex, which in turn interacts strongly with .NO, forming a stable and water-soluble complex in aqueous solution, i.e., [(MGD)$_2$/Fe-NO] complex (see, for example, Lai and Komarov, in FEBS Letters, 345:120–124, 1994; Komarov and Lai, in Biochim. Biophys. Acta, 1272:29–36, 1995). The latter complex gives rise to a sharp three-line spectrum with $g_{iso}$=2.04, characteristic of a nitrosyl-Fe-dithiocarbamate complex which can readily be detected by EPR spectroscopy at ambient temperature.

Presently preferred dithiocarbamates for use herein include compounds having the structure:

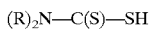

(R)$_2$N—C(S)—SH     (I)

wherein:
  each R is independently selected from a C$_1$ up to C$_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or the like, or the two R groups can cooperate to form a 5-, 6- or 7-membered ring including N and the two R groups, or
  either of the R groups is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "alkenyl" refers to straight or branched chain hydrocarbyl groups having at least one carbon—carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon—carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "acyl" refers to alkyl-carbonyl species.

As employed herein, "halogen" refers to fluoride, chloride, bromide or iodide atoms.

Presently preferred dithiocarbamates contemplated for use in the practice of the present invention are compounds having the structure I, wherein:
  one of the R groups is selected from a C$_1$ up to C$_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfiryl, while
  the other R group is selected from a C$_1$ up to C$_4$ alkyl or substituted alkyl.

Especially preferred dithiocarbamates contemplated for use in the practice of the present invention are compounds having the structure I, wherein:
  one of the R groups is selected from a C$_2$ up to C$_8$ alkyl or substituted alkyl, wherein the substituents are selected from carboxyl, acetyl, pyridinyl, pyrrolidinyl, amino, amido, hydroxy or nitro, while
  the other R group is selected from methyl, ethyl, propyl or butyl.

The presently most preferred dithiocarbamates contemplated for use in the practice of the present invention are compounds having the structure I, wherein:
  one of the R groups is selected from a C$_2$ up to C$_8$ alkyl or substituted alkyl, wherein the substituents are selected from carboxyl, acetyl, amido or hydroxy, while the other R group is selected from methyl, ethyl, propyl or butyl.

A wide variety of non-targeting, non-immunogenic macromolecules other than antibodies can be employed in the practice of the present invention, such as, for example polypeptides, polysaccharides, polynucleic acids, and the like. Macromolecules contemplated for use herein can be synthetic, naturally occurring or modified naturally occurring materials and are preferably non-immunogenic.

Polypeptides contemplated for use herein include naturally occurring proteins (such as serum albumin, and the like), purified protein derivatives (e.g., a purified protein derivative of tuberculin), recombinant proteins, modified proteins (e.g., cationized albumin), and the like.

A presently preferred protein contemplated for use in the practice of the present invention is albumin. Albumin protein naturally present in the circulation serves as a carrier for metals, ions, fatty acids, amino acids, bilirubin, enzymes, drugs, and the like. In normal adult humans, plasma albumin levels are about 3.5–5.0 g/dL (see, for example, Halliwell, in Biochem. Pharmacol., 37:569–571, 1988). Since the capillary walls are relatively impermeable to proteins in the plasma, proteins (including albumin) therefore exert an osmotic force (or oncotic pressure) of about 25 mm Hg across the capillary wall. This force tends to pull water into the blood.

High serum albumin levels (within the normal range) have been associated with decreased incidences of stroke and coronary heart diseases (see, for example, Aptaker et al., in Arch. Phys. Med. Rehabil., 75:80–84, 1994). Not surprisingly, therefore administration of albumin solution has been shown to exert some beneficial effects in animals and patients with ischemic stroke, presumably acting by diminishing the bulk flow through the disrupted blood-brain barrier and ameliorating the vasogenic edema (see, for example, Matsui et al., in Neurosurgery, 33:293–300, 1993). In addition, albumin has been shown to act as an antioxidant which reacts and neutralizes reactive oxygen species (see, Halliwell, in supra). In view of these known beneficial effects of albumin, the combination of albumin with dithiocarbamates, which have separately been shown to impart substantial therapeutic effects, produces a very useful diagnostic and therapeutic agent.

Polysaccharides contemplated for use herein include dextran, hyaluronic acid, cellulose, starch, glycogen, and the like.

Polynucleic acids contemplated for use herein include naturally occurring double strand DNA, single strand DNA, RNA, synthetic DNA, recombinant DNA, recombinant RNA, and the like.

Crosslinking contemplated by the invention method can be carried out in a variety of ways, i.e., the dithiocarbamate can be crosslinked to a non-targeting macromolecule other than an antibody by a crosslinking agent via any functionality on the macromolecule. Exemplary functionalities on said macromolecule include amino groups, hydroxy groups, sulfhydryl groups, carboxyl groups, and the like. However, since it is well known that dithiocarbamates decompose readily under acidic conditions, to prevent decomposition of the dithiocarbamate, the pH of the cross-linking reaction generally falls in the range from about 6.0 to about 7.0.

Crosslinking agents contemplated for use herein include photoreactive crosslinkers, homobifinctional crosslinkers, heterobifinctional crosslinkers, and the like. Examples of photoreactive crosslinkers are azido compounds, diazo compounds, and the like.

Exemplary azido and diazo compounds include sulfosuccinimidyl (4-azidosalicylamido)hexanoate, azido-benzoyl hydrazide, N-5-azido-2nitrobenzoyloxysuccinimide, N-4-(p-azido-salicylamido)butyl-3'(2'-pyridyldithio) propionamide, p-azidophenylglyoxal monohydrate, 4-(p-azidosalicylamido) 4-(iodoacetamido)butane, bis[(β-4-azidosalicylamido)ethyl]disulfide, N-hydroxy-succinimidyl 4-azidobenzoate, N-hydroxysulfosuccininidyl 4-azidobenzoate, N-hydroxysuccinimidyl-4-azidosalicylic acid, N-hydroxysul-fosuccinimidyl-4-azidosalicylicacid, p-nitrophenyl-2-diazo-3,3,3-trifluoropropionate, 2-diazo-3,3,3-trifluorpropionyl chloride, N-succinimidyl-(4-azidophenyl)-1,3'-dithiopropionate, sulfosuccinimidyl(4-azidophenyldithio)propionate, sulfosuccinimidyl-2-(7-azido-4-methylcoumarin-3-acetamide) ethyl-1,3'-dithiopropionate, sulfosuccinimidyl-7-azido-4-methylcoumarin-3-acetate, sulfosuccinimidyl-2-(m-azido-o-nitrobenzamido)-ethyl-1,3'-dithiopropionate, and the like.

Bifunctional crosslinkers contemplated for use herein can be further divided into two categories, i.e., homobifinctional crosslinkers and heterobifunctional crosslinkers.

Exemplary homobifunctional crosslinkers include dimethyl adipimidate, dimethyl suberimidate, dimethyl pimilimidate, disuccinimidyl glutarate, disuccinimidyl suberate, bis(sulfosuccinimidyl) suberate, bis(diazobenzidine), ethylene glycobis(succinnimdylsuccinate), disuccinimidyl tartrate, disulfosuccinimidyl tartrate, bismaleidohexane, glutaraldehyde, dithiobis(succinimidyl propionate), dithiobis(sulfosuccinimidyl propionate), 1,4-di [3',2'-pyridyldithio(propionamido) butane], N,N'-dicyclohexylcarbodiimide, bis[2-(succinimidyloxycarbonyloxy)ethyl]sulfone, dimethyl 3,3'-dithiobispropionimidate, and the like.

Exemplary heterobifunctional crosslinkers include succinimidyl 4-(N-maleimidomethyl)cyclohexane-1-carboxylate, m-maleimidobenzoyl-N-hydroxysuccinimide ester, succinimidyl-4-(p-maleimidophenyl)butyrate, N-(γ-maleimido-butyryloxy)succinimide ester, N-succinimidyl (4-iodoacetyl) aminobenzoate, 4-succinimidyl oxycarbonyl-α-(2-pyridyldithio)toluene, sulfosuccinimidyl-6-[α-methyl-α-(2-pyridyldithio) toluamido]hexanoate, N-succinimidyl-3-(2-pyridyldithio) propionate, 3-(2-pyridyldithio) propionyl hydrazide, 1-ethyl-3-(3-dimethylaminopropyl) carbodimide hydrochloride, 3-(p-azidosalicylamido) butylamine, 1,5-difluoro-2,4-dinitrobenzene, N-hydroxysuccinimidyl 2,3-dibromo-propionate, and the like.

When photoreactive crosslinking agents are employed, typical crosslinking conditions comprise exposure to ultraviolet radiation at a temperature in the range of about 4° C. up to about 40° C. for a time in the range of about 0.1 min up to about 10 min.

When bifunctional crosslinking agents are employed, typical crosslinking conditions comprise first contacting the crosslinking agent with either the dithiocarbamate or the macromolecule at a temperature in the range of about 4° C. up to about 40° C. for a time in the range of about 0.1 min up to about 30 min; then subsequently contacting the resulting intermediate with the other of the dithiocarbamate or the macromolecule (whichever was not employed in the initial contacting) at a temperature in the range of about 4° C. up to about 40° C. for a time in the range of about 0.1 min up to about 30 min.

In accordance with a still further embodiment of the present invention, there are provided methods to obtain in vivo magnetic resonance images which involve administering iron-containing contrast agent compositions as described herein to a subject, and then imaging said subject.

The breakdown of the blood-brain barrier is known to occur as a result of cerebral stroke. This leads to a significant increase in permeability, which would permit the diffusion of non-immunogenic macromolecules other than antibodies (such as the iron-containing derivatives of the dithiocarbamate-macromolecule-containing compositions of the invention) into the infarcted cerebral tissues. Due to the inherent paramagnetic properties of such compositions, the distribution thereof in the brain (as well as the volume of the infarcted region) can readily be assessed by MRI techniques.

In accordance with a further embodiment of the present invention, there are provided methods for the treatment of subjects suffering from a wide range of disease states and/or indications, such as, for example, septic shock, ischemia, administration of cytokines, overexpression of cytokines, ulcers, inflammatory bowel disease (e.g., gastritis, ulcerative colitis or Crohn's disease), diabetes, arthritis (e.g., rheumatoid arthritis), asthma, Alzheimer's disease, Parkinson's disease, multiple sclerosis, cirrhosis, allograft rejection (e.g., transplant rejection), encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, age-related macular degeneration, optic neuritis, and the like), ileitis, inflammation induced by overproduction of inflammatory cytokines (e.g., liver inflammation, renal inflammation, airway inflammation, and the like), hemorrhagic shock, anaphylactic shock, burn, infection leading to the overproduction of inflammatory cytokines (including bacterial (e.g., E. coli infection), viral (e.g., HIV), fungal (e.g., Candidiosis and histoplasmosis) and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, neurodegenerative disorders (e.g., chronic neurodegenerative disease), chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), druginduced lung injury (e.g., paraquat), transplant rejection and preservation, fertility enhancement, bacterial translocation, circulatory shock, traumatic shock, photoaging, photodamage, and the like.

A presently preferred indication for treatment in accordance with the present invention is cardiovascular disease, which can be treated by administering to a subject in need thereof an effective amount of dithiocarbamate-macromolecule-containing compositions as described herein. As used herein, the term "cardiovascular disease" includes stroke, heart failure, renal failure, ischemia/reperfusion injury, head injury, and the like.

As readily recognized by those of skill in the art, invention compositions are amenable to a variety of modes of delivery, e.g., oral delivery, transdermal delivery, intravenous delivery, intramuscular delivery, topical delivery, nasal delivery, and the like. Depending on the mode of delivery employed, the dithiocarbamate-macromolecule-containing composition can be delivered in a variety of pharmaceutically acceptable forms. For example, the composition can be delivered in the form of a solid, solution, emulsion, dispersion, micelles, liposome, and the like.

Pharmaceutically acceptable forms of invention compositions include solids, solutions, emulsions, dispersions, micelles, liposomes, and the like, wherein the resulting formulation contains one or more of the compositions of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active composition is included in the pharmaceutical formulation in an amount sufficient to produce the desired effect upon the process or condition being treated.

Pharmaceutical formulations containing the invention composition may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known to the art for the manufacture of pharmaceutical formulations and such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical formulations may be in the form of a sterile injectable suspension. This suspension may be formulated according to known methods using is suitable dispersing or wetting agents and suspending agents. The sterile injectable preparation may also be a sterile injectable solution or suspension in a non-toxic parenterally-acceptable diluent or solvent, for example, as a solution in 1,3-butanediol.

Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compositions may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly. Typical daily doses, in general, lie within the range of from about 80 $\mu$g up to about 300 mg per kg body weight, and, preferably within the range of from 100 $\mu$g to 10 mg per kg body weight and can be administered up to four times daily. The typical daily IV dose lies within the range of from about 10 g to about 100 mg per kg body weight, and, preferably, within the range of from 50 $\mu$g to 10 mg per kg body weight.

In accordance with yet another embodiment of the present invention, there are provided methods for the treatment of iron overload, said method comprising administering to said subject an effective amount of dithiocarbamate-macromolecule-containing compositions as described herein. Iron overload includes such conditions as hemochromatosis, hereditary hemochromatosis, hereditary spherocytosis, hemodialysis, thalassemia, blood transfusion (or hemosiderosis), repeated blood transfusions, anemia, sickle cell anemia, dietary iron uptake, latrogenic iron uptake, intramuscular iron dextran, hemolytic disease of the newborn, and the like.

In accordance with yet another embodiment of the present invention, there are provided methods for the treatment of non-iron overload diseases and conditions, said method comprising administering to said subject an effective amount of dithiocarbamate-macromolecule-containing compositions as described herein. Non-iron overload diseases and conditions contemplated for treatment herein include inflammation, ischemia/reperfusion injury, cancers, malaria, renal failure, Alzheimer's disease, Parkinson's disease, heart disease, AIDS, liver disease, infection, lung injury, graft-versus-host disease, transplant rejection and preservation, and the like.

As readily understood by those of skill in the art, a wide variety of agents and/or conditions induce expression of inducible nitric oxide synthase, and hence the potential negative impact of such exposure can be ameliorated by the combinational approach described herein. Thus, for example, exposure to cytokines, cytokine receptors, endotoxins, platelet activating factors, bradykinins, bradykinin receptors, bacteria, parasites, viruses, coagulation factors, arachidonate metabolites, nitric oxide synthase, nuclear factor kappa B, ultraviolet light, gamma ray irradiation, elevated temperature, oxygen radicals, and the like, can advantageously be circumvented by using the combinational approach described herein.

Induction of expression of inducible nitric oxide synthase, and hence, overproduction of nitric oxide, is associated with a wide range of disease states and/or indications, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., gastritis, ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, agerelated macular degeneration, optic neuritis, and the like), ileitis, inflammation (e.g., liver inflammation, renal inflammation, airway inflammation, and the like), bum, infection (including bacterial (e.g., E. coli infection), viral (e.g., HIV), fungal (e.g., Candidiosis and histoplasmosis) and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, adult respiratory distress syndrome, cachexia, myocarditis, autoimmune disorders, eczema, psoriasis, heart failure, atherosclerosis, dermatitis, urticaria, systemic lupus erythematosis, AIDS, AIDS dementia, neurodegenerative disorders (e.g., chronic neurodegenerative disease), chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), mlyasthenia gravis (MG), transplant rejection and preservation, fertility enhancement, bacterial translocation, circulatory shock, traumatic shock, photoaging, photodamage, and the like.

Treatment of such conditions can be carried out with a variety of reagents, such as, for example, inhibitors of cytokine synthesis/release (e.g., anti-cytokine antibodies, anti-cytokine receptor antibodies, and the like), anti-endotoxin antibodies, bradykinin antagonists, synthetic peptide blocking bradykinin receptors, bactericidal/permeability increasing protein, inhibitors of the coagulation cascade (e.g., antibodies to platelet activating factor), inhibitors of complement activation, inhibitors of arachidonate metabolism, inhibitors of nitric oxide synthase enzymes, immunosuppressors, diabetic therapeutic agents, anti-inflammatories, agents useful for stroke therapy, agents useful for asthma therapy, agents useful for cirrhosis therapy, anti-cancer therapeutics, anti-microbial therapeutics, anti-fungal therapeutics, anti-retroviral therapeutics, agents useful for the treatment of opportunistic infections and malignancies, agents useful for the treatment of Lupus erythmatosus, agents useful for the treatment of uveitis, thrombolytic agents, antispasmodic agents, antidiarrheal agents, agents useful for the treatment of constipation, antihistamines, agents useful for the treatment of Parkinson's disease, therapeutic agents for Crohn's disease therapy, anti-oxidants, and the like.

Such agents, employed either alone or as part of a combination of any two or more thereof, can advantageously be combined with dithiocarbamate-containing nitric oxide scavengers as described herein, and can be used for a variety of indications, such as for example, anti-endotoxin therapy (e.g., antibodies to endotoxin, antibodies to LPS-binding protein, soluble CD14 protein, bactericidal/permeability increasing protein, polymyxin B, and the like), inhibition of cytokine synthesis/release (e.g., employing phosphodiesterase inhibitors, IL-4, IL-10, IL-13, TGF-β, corticosteroids, and the like), anti-cytokine therapy (e.g., employing antibodies to TNF, soluble JNF receptors, IL-1 receptor antagonists, antibodies to IL-1 receptors, antibodies to IL-6, antibodies to interferon-γ, soluble interferon-γ receptors, and the like), inhibition of the coagulation cascade (and of complement activation, employing such agents as anti-Factor XII antibodies, antibodies to C5a, C1-esterase inhibitors, soluble Cr1, and the like), inhibition of platelet activating factor (PAF, employing such agents as PAF receptor antagonists, and the like), inhibition of arachidonate metabolism (e.g., employing agents such as cyclooxygenase inhibitors, lipoxygenase inhibitors, leukotriene inhibitors, thromboxane $A_2$ inhibitors, prostaglandins, and the like), inhibition of nitric oxide synthase enzymes (e.g., employing arginine analogs (such as L-$N^G$-methylarginine, L-$N^G$-nitroarginine, L-$N^G$-aminoarginine, L-iminoethylornithine, ε-N-iminoethyl-L-lysine, L-$N^G$-nitroarginine methyl ester, L-$N^G$-hydroxyl-$N^G$-methylarginine, L-$N^G$-methyl-$N^G$-methylarginine, L-thiocitrulline, L-S-methylthiocitrulline, L-S-ethylisothiocitrulline, S-ethylisothiocitrulline, aminoguanidine, S-methyl isothiourea sulfate, and the like), heme ligands (such as 7-nitroindazole, 7,7,8,8-tetramethyl-o-quinodimethane, imidazole, 1-phenylimidazole, 2-phenylimidazole, and the like), calmodulin antagonists (such as chlorpromazine, W-7, and the like), and the like);

immunosuppression (e.g., employing one or more agents such as cyclosporin A, OKT3, FK506, mycophenolate mofetil (MMF), azathioprine, corticosteroids (such as prednisone), antilymphocyte globulin, antithymocyte globulin, and the like), diabetic therapy (e.g., employing one or more agents such as free pancreatic islets, encapsulated pancreatic islets, oral insulin, intravenous insulin, amylin hormone, and the like), dihydropyridine calcium channel blockers (e.g., employing agents such as nifedipine, nitrendipine, nisoldipine, and the like), acetohexamide, chlorpropamide, glyburide, glipizide, metfornin, tolbutamide, tolazamide, and the like, inflammatory disease therapy (e.g., employing disease-modifying agents (such as antimalarials, methotrexate, sulfasalazine, mesalamine, azathioprine, 6-mercaptopurine, metronidazole, injectable and oral gold, D-penicillamine, and the like), corticosteroids, non-steroidal antiinflammatory drugs (such as acetominophen, aspirin, sodium salicylate, magnesium salicylate, choline magnesium salicylate, salicylsalicylic acid, ibuprofen, naproxen, diclofenac, diflunisal, etodolac, fenoprofen calcium, fluriprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, tolmetin, and the like), and the like), stroke therapy (e.g., employing one or more agents such as fibrinolytic agents (such as streptokinase, acylated plasminogen-streptokinase complex, urokinase, tissue plasminogen activator, and the like), employing monoclonal antibodies directed against leukocyte adhesion molecules (such as intercellular adhesion molecule-1 (ICAM-1), CD18, and the like), hemodilution therapy (employing modified hemoglobin solutions such as diaspirin crosslinked hemoglobin), employing growth factors (such as basic fibroblast growth factor (bFGF), transforming growth factor-beta 1 (TGF-β1), and the like), employing glutamate antagonists (such as lamotrigine, dizolcilpine maleate (MK 801), BW619C89, BW1003C87, and the like), employing NMDA antagonists (such as CGS 19755 (Selfotel), aptiganel hydrochloride, dextrorphar, d-CPPene, and the like), employing GABA agonists (such as muscimol), employing free radical scavengers (such as allopurinol, S-PBN, 21-aminosteroids, tocopherol, superoxide dismutase, dexanabinol (HU-211), selenium, carotenoids, and the like), idebenone, ticlopidine, lovastatin, citicoline, and the like), asthma therapy (e.g., employing bronchodilators (such as albuterol, salmeterol, metaprotemol, bitolterol, pirbuterol, terbutaline, isoproterenol, epinephrine, and the like), theophyllines (such as theophylline, aminophylline, and the like), corticosteroids (such as beclomethasone, prednisone, and the like), antimediators (such as cromolyn sodium, nedocromil sodium, and the like), and the like), cirrhosis therapy (e.g., employing diuretics (such as spironolactone), opiate antagonists (such as naloxone), cholestyramine, colchicine, colestipol, methotrexate, rifampin, ursodeoxycholic acid, and the like, anti-cancer therapy (e.g., employing one or more agents such as alkylating agents (such as mechlorethamine, chlorambuccil, ifosfamide, melphalan, busulfan, carmustine, lomustine, procarbazine, dacarbazine, cisplatin, carboplatin, and the like), antimetabolites (such as methotrexate, mercaptopurine, thioguanine fluorouracil, cytarabine, and the like), hormonal agents (such as testosterone propionate, fluoxymesterone, flutamide, diethylstilbestrol, ethinyl estradiol, tamoxifen, hydroxyprogesterone caproate, medroxyprogesterone, megestrol acetate, and the like), adrenocorticosteroids (such as prednisone), aromatase inhibitors (such as amino glutethinide), leuprolide, goserelin acetate, biological response modifiers (such as interferon-α2a, interferon-α2b, interleukin-2, and the like), peptide hormone inhibitors (such as octreotide acetate), natural products (such as vinblastine, vincristine, vinorelbine, paclitaxel, dactinomycin, daunorubicin, idarubicin, doxorubicin, etoposide, plicamycin, mitomycin, mitoxantrone, bleomycin, hydroxyurea, mitotane, fludarabine, cladribine, and the like), supportive agents (such as allopurinol, mesna, leucovorin, erythropoietin, filgrastim, sargramostim, and the like), and the like, anti-microbial therapy (e.g., employing one or more agents such as celftriaxone, TMP-SMZ, penicillin, aminoglycosides, vancomycin, gentamicin, rifampin, imipenem, clindamycin, metronidazole, tetracycline, erythromycin, sulfonamide, streptomycin, ampicillin, isoniazid, pyrazinamide, ethambutol, and the like), anti-fungal therapy (e.g., employing agents such as amphotericin B, griseofulvin, myastatin, flucytosine, natamycin, antifungal imidazoles (e.g., clotrimazole, miconazole, ketoconazole, fluconazole, itraconazole, and the like), and the like, anti-retroviral therapy (e.g., employing agents such as protease inhibitors (such as Invirase, Ritonavir, Crixivan, and the like), zidovudine, didanosine, zalcitabine, stavudine, viramune, and the like)

treatment of opportunistic infections and malignancies (e.g., anti-AIDS treatment, employing agents such as pentamidine, trimethoprim/sulfamethoxazole, primaquine, atovaquone, clarithromycin, clofazimine, ethambutol, rifampin, amikacin, ciprofloxacin, pyrimethamine, amphotericin B, ganciclovir, foscarnet, fluconazole, ketoconazole, acyclovir, and the like), Lupus erythymatosus therapy (e.g., employing agents such as hydroxychloroquine sulfate, chloroquine sulfate, quinacrine, dapsone, isotretinoin, and the like), uveitis therapy (e.g., employing agents such as corticosteroids, azathioprine, cyclosporine, and the like), thrombolytic therapy for acute myocardial infarction (e.g., employing agents such as streptokinase, tissue plasminogen activator (t-PA), anistreplase, and the like), antispasmodic treatment (e.g., employing agents such as dicyclomine, hyoscyamine, propantheline, and the like), antidiarrheal treatment (e.g., employing agents such as loperamide, diphenoxylate with atropine, and the like), anticonstipation treatment (e.g., employing agents such as fiber supplementation with bran, psyllium, methylcellulose, polycarbophil, cisapride, and the like), antihistamine therapy (e.g., employing agents such as ethanolamines (such as diphenhydramine, clemastine, and the like), ethylenediamines (such as brompheniramine, chlorpheniramine, triprolidine, and the like), phenothiazines (such as hydroxyzine), piperidines (such as terfenadine, astemizole, azatadine, cyproheptadiene, loratidine, and the like), and the like), anti-Parkinsonian therapy (e.g., employing agents such as benztropine mesylate, biperiden, chlorphenoxamine, cycrimine, orphenadrine, procyclidine, trihexyphenidyl, and the like), as well as other indications which involve the induction of nitric oxide synthase, as can readily be identified by those of skill in the art.

In addition, co-administration of therapeutic agents suitable for treatment of a wide variety of diseases and conditions, in combination with dithiocarbamate-containing nitric oxide scavenger(s) as described herein, is contemplated by the present invention.

For example, invention dithiocarbamate-containing nitric oxide scavenger(s) are advantageously employed in conjunction with the administration of immunosuppressants, such as glucocorticoids (methylprednisolone), myelin basic protein (e.g., 7-capaxone), anti-Fc receptor monoclonal antibodies, hydroorotate dehydrogenase inhibitor, anti-IL2 monoclonal antibodies (e.g., dacliximab), buspirone, castanospermine, CD-59 (complement factor inhibitor), 5-lipoxygenase inhibitor, phosphatidic acid synthesis antagonists, ebselen, edelfosine, enlimomab, galaptin, platelet activating factor antagonists, selectin antagonists, interleukin-10 agonist, macrocylic lactone, methoxatone, mizoribine, protein kinase C inhibitors, phosphodiesterase IV inhibitor, sialophorin, sirolimus, spirocyclic lactams, 5-hydroxytryptamineantagonist, and the like.

Additional treatments for which invention dithiocarbamate-containing nitric oxide scavenger(s) are advantageously employed in conjunction with the primary treating agent include administration of antimetabolite cytotoxics (e.g., azathioprine, cyclophosphamide), C5a release inhibitor, benzydamine, peldesine, pentostatin, thalidomide, benzoporphyrin derivatives, arachidonate antagonists (e.g., halometasone, halobetasol propionate), corticosteriod (clobetasol propionate), growth hormone antagonists (octapeptide somatostatin analogue, lanreotide, angiopeptin and dermopeptin), thymopentin, and the like.

Other treatments for which invention dithiocarbamate-containing nitric oxide scavenger(s) are advantageously employed in conjunction with the primary treating agent include administration of neuroprotective agents, such as α-adrenoreceptor antagonist (e.g., α-dihydroergocryptine), NMDA antagonists (e.g., remacemide, 2-piperazinecarboxylic acid, N-indologlycinamide derivatives, spiro[benzo(b)thiophen-4(5H)]derivatives, eliprodil, dexanabinol, amantadine derivatives, dizocilpine, benzomorphan derivatives, aptiganel, (S)-α-phenyl-2-pyridine ethanamide dihyrochloride, 1-amninocyclopentanecarboxylic acid, and the like), sodium channel antagonists, glycine antagonists (e.g., glystasins), calcium channel antagonists (e.g., 3,5-pyridinedicarboxylic acid derivatives, conopeptides, 1-piperazineethanol, thieno[2,3-b]pyridine-5-carboxylic acid derivatives, nilvadipine, nisoldipine, tirilazad mesylate, 2H-1-enzopyran-6-ol, nitrone spin traps, iacidipine, iomeerzine hydrochloride, lemildipine, lifarizine, efonidipine, piperazine derivatives, and the like), calpain inhibitors, fibrinogen antagonists (e.g., ancrod), integrin antagonists (e.g., antegren), thromboxane $A_2$ antagonist (e.g., 9H-carbazole-9-propanoic acid derivatives, 5-Heptenoic acid derivatives, 1-azulenesulfonic acid derivatives, and the like), brainderived neurotropic factor, adrenergic transmitter uptake inhibitor (e.g., 1-butanamine), endothelin A receptor antagonists (e.g., benzenesulfonamide derivatives), GABA A receptor antagonists (e.g., triazolopyrimidine derivatives, cyclohexaneacetic acid derivatives, and the like), GPIIb IIIa receptor antagonists, platelet aggregation antagonist (e.g., 2(1H)-quinolinone derivatives, 1H-pyrrole-1-acetic acid derivatives, coumadin, and the like), Factor Xa inhibitor, corticotropin releasing factor agonist, thrombin inhibitor (e.g., fraxiparine, dermatan sulfate, heparinoid, and the like), dotarizine, intracellular calcium chelators (e.g., BAPTA derivatives), radical formation antagonists (e.g., EPC-K1,3-pyridinecarboxamide derivatives, superoxide dismutase, raxofelast, lubeluzole, 3H-pyrazol-3-one derivatives, kynurenic acid derivatives, homopiperazine derivatives, polynitroxyl albumin, and the like), protein kinase inhibitors (e.g., 1H-1,4-diazepine), nerve growth agonist, glutamate antagonist (e.g., cyclohexanepropanoic acid, riluzole, acetamide derivatives, and the like), lipid peroxidase inhibitors (e.g., 2,5-cyclohexadiene-1,4-dione derivatives), sigma receptor agonist (e.g., cyclopropanemethanamine derivatives), thyrotropin releasing hormone agonist (e.g., L-prolinamide, posatirelin, and the like), prolyl endopeptidase inhibitor, monosialoganglioside GM1, proteolytic enzyme inhibitor (e.g., nafamostat), neutrophil inhibitory factor, platelet activating factor antagonist (e.g., nupafant), monoamine oxidase B inhibitor (e.g., parafluoroselegiline, benzonitrile derivatives, and the like), PARS inhibitors, Angiotensin I converting enzyme inhibitor (e.g., perindopril, ramipril, and the like), acetylcholine agonist (e.g., pramiracetam), protein systhesis antagonist (e.g., procysteine), phosphodiesterase inhibitor (e.g., propentofylline), opioid kappa receptor agonist (e.g., 10H-phenothiazine-2-carboxamine derivatives), somatomedin-1, carnitine acetyltransferase stimulant (e.g., acetylcarnitine), and the like.

Still further treatments for which invention dithiocarbamate-containing nitric oxide scavenger(s) are advantageously employed in conjunction with the primary treating agent include administration of T cell inhibitors, such as synthetic leucocyte antigen derived peptides, interleukin-1 receptor antagonist, MG/AnergiX, anti-CD3 monoclonal antibodies, anti-CD23 monoclonal antibodies, anti-CD28 antibodies, anti-CD2 monoclonal antibodies, CD4 antagonists, anti-E selectin antibodies, MHC inhibitors, mycophenolate mofetil, and the like.

Additional treatments for which invention dithiocarbamate-containing nitric oxide scavenger(s) are advantageously employed in conjunction with the primary treating agent include administration of antimigraine agents, such as naratriptan, zolmitriptan, rizatriptan, quetiapine, Phytomedicine, (S)-fluoxetine, calcium channel antagonists (e.g., nimodipine/Nimotop, flunarizine, dotarizine, iomerizine HCl, and the like), α-dihydroergocryptine, 5-HT1 agonists, (e.g., Sumatriptan/Imitrex, Imigran, and the like), 5-HT1D agonists, 5-HT1A antagonists, 5-HT1B antagonists, 5-HT1D antagonists (e.g., 1H-indole-5-ethanesulfonamide derivatives, 1H-indole-5-methanesulfonamide, and the like), 2-thiophenecarboxamide, 3-piperidinamine, diclofenac potassium, dihydroergotamine, dolasetron mesilate, dotarizine, flupirtine, histamine-H3 receptor agonist, indobufen, 1-azulenesulfonic acid derivatives, cholinesterase inhibitors, bradykinin antagonists, substance P antagonists (e.g., Capsaicin/Nasocap), piperazine derivatives, neurokinin 1 antagonists, metergoline, dopamine D2 antagonist (e.g., metoclopramide+lysine acetyl), enkephalinase inhibitors (e.g., neutral endopeptidase), 5-HT2 antagonists, 5-HT3 antagonists (e.g., Dolasetron mesilate, 4H-carbazol-4-one derivatives, and the like), tenosal, tolfenamic acid, cyclooxygenase inhibitors (e.g., carbasalate/carbaspirin calcium, tenosal, and the like), alpha adrenoreceptor antagonists (e.g., arotinolol, dihydroergocryptine, and the like), opioid agonists (e.g., flupirtine), beta adrenergic antagonists (e.g., propranolol), valproate semisodium, and the like.

Additional treatments for which invention dithiocarbamate-containing nitric oxide scavenger(s) are advantageously employed in conjunction with the primary treating agent include administration of antiarthritic agents, such as anti-CD4 monoclonal antibodies, phospholipase A1 inhibitor, loteprednol, tobramycin, combination of loteprednol and tobramycin, salnacedin, amiprilose, anakinra, anergiX, anti-B7 antibody, anti-CD3H, anti-gp39, anti-MHC MAbs, antirheumatic peptides, anti-Tac(Fv)-PE40, AP-1 inhibitors, purine nucleotide phosphorylase inhibitors, bindarit, CD2 antagonist, campath-1H, CD4 antagonist, tumor necrosis factor antagonist (e.g., p80 TNFR, rhTNFbp, peptide T, CenTNF, thalidomide, and the like), cobra venom factor, interleukin la agonist (e.g., cytogenin), interleukin 2 receptor antagonist (e.g., dacliximab), ICAM 1 antagonist (e.g., enlimomab), interleukin 1 beta converting enzyme inhibitors (e.g., ICE-inhibitors), interferons, interleukin-10, interleukin 1 antagonist, interleukin 2 antagonist (e.g., sirolimus), phospholipase C inhibitor, neurokinin 1 antagonist, laflunimus, leflunomide, leucotriene antagonists, levamisole, LFA3TIP, macrocyclic lactone, MHC class II inhibitors, mizoribine, mycophenolate mofetil, NFκB inhibitors, peldesine, pidotimod, PNP inhibitors, reumacon, CD28 antagonist, roquinimex, subreum, tacrolimus, transforming growth factor beta agonist, methionine synthase inhibitors (e.g., vitamin B12 antagonist), adenosine A2 receptor agonist, CD5 antagonist (e.g., zolimomab), 5-lipoxygenase inhibitor (e.g., zileuton, tenidap, and the like), cyclooxygenase inhibitor (e.g., tenoxicam, talmetacin, piroxicam cinnamate, oxaprozin, mofezolac, nabumetone, flurbiprofen, aceclofenac, diclofenac, dexibuprofen, and the like), metalloproteinase inhibitor (e.g., TNF convertase inhibitors), phospholipase A2 inhibitor, leucotriene B4 antagonist, collagenase inhibitor, cyclooxygenase 2 inhibitor (e.g., meloxicarn), thromboxane synthase inhibitor (e.g., curcumin), cysteine protease inhibitor, metalloproteinase inhibitor, lipocortins synthesis agonist (e.g., rimexolone, predonisolone 21-farnesylate, deflazacort, and the like), chelating agent (e.g., diacerein), elastase inhibitors, nitric oxide antagonists (e.g., hydroxocobalamin), stromelysin inhibitors, prostaglandin E1 agonist (e.g., misoprostol, misoprostol+diclofenac, and the like), dihydrofolate reductase inhibitor (e.g., trimetrexate), opioid antagonist (e.g., nalmefene), corticotropin releasing factor antagonist, proteolytic enzyme inhibitor (e.g., protease nexin-1), bradykinin antagonist (e.g., tachykinin antagonists), growth hormone antagonist (e.g., octreotide), phosphodiesterase IV inhibitor, gelatinase inhibitor, prostaglandin synthase inhibitors (e.g., sulfasalazine), and the like.

Additional treatments for which invention dithiocarbamate-containing nitric oxide scavenger(s) are advantageously employed in conjunction with the primary treating agent include administration of agents useful for the treatment of septic shock, such as angiogenesis inhibitors, bradykinin antagonists, complement factor inhibitors (e.g., C3 convertase inhibitor), C5a release inhibitors, dopamine agonists (e.g., dopexamine), elastase inhibitors, E selectin antagonists, famesyltransferase inhibitors (e.g., RBE limonene), immunostimulants (e.g., lipid A vaccine, edobacomab, nebacumab, StaphGAM, diabodies, and the like), immunosuppressants (e.g., transcyclopentanyl purine analogues), interleukin 1 antagonists (e.g., interleukin 1 receptors), interleukin 1 receptor antagonists (e.g., anakinra), interleukin 1b antagonists (e.g., interleukin-1 β), interleukin 1 beta converting enzyme inhibitors (e.g., ICE-inhibitors), interleukin 8 antagonists (e.g., IL-8 receptor), interleukin 13 agonists (e.g., intereleukin-13), lipase clearing factor inhibitors, membrane permeability enhancers (e.g., Bactericidal Permeability Increasing protein/BPI), nitric oxide synthase inhibitors (e.g., L-NMMA, a-methyl-N-iminoethyl-ornithine, and the like), P2 receptor stimulants (e.g., ATP analogues), phosphatidic acid synthesis antagonists (e.g., lisofylline), phospholipase A2 inhibitors (e.g., acylpyrrole-alkanoic acid derivatives, indoleacetic acid derivatives, and the like), platelet activating factor antagonists (e.g., (2RS,4R)-3-(2(3-pyridinyl)thiazolidin-4-oyl) indoles), prostacyclin agonists (e.g., taprostene), protein kinase C inhibitors, selectin antagonists (e.g., sulfated glycolipid cell adhesion inhibitors), TNF receptor-Ig, tumor necrosis factor antagonists (e.g., anti-TNF MAbs), tumor necrosis factor alpha antagonists, and the like.

Still further treatments for which invention dithiocarbamate-containing nitric oxide scavenger(s) are advantageously employed in conjunction with the primary treating agent include administration of agents for the treatment of multiple sclerosis, such as 4-aminopyridine, deoxyspergualin, ACTH, amantadine, antibody adjuvants (e.g., poly-ICLC), anti-cytokine monoclonal antibodies, anti-inflammatory agents, bacloten, bethanechol chloride, carbamazepine, carbohydrate drugs, clonazepam, CNS and immune system function modulators, cyclophosphamide, cyclosporine A, cytokines (e.g., IFN-α, alfaferone, IFN-β 1b, betaseron, TGF-β2, PEG-TGF-β2, betakine, IFN-β/Rebif, frone, interferon-β, IFN-β, and the like), CD4+T cell inhibitors (e.g., AnergiX), CD28 antagonists, growth factors (e.g., glial growth factor, GGF, nerve growth factors, TGF-β2, PEG-TGF-β2, betakine, and the like), humanized MAb (e.g., anti-IFN-γMAb, smart anti-IFN-γMAb, anti-Tac antibody, smart anti-Tac antibody, and the like), humanized anti-CD4 MAb (e.g., anti-CD4 MAb, centara, and the like), hydrolase stimulants (e.g., castanospermine), IFN-α, IFN-γ antagonists (e.g., anti-IFN-γMAb, smart anti-IFNγMAb, and the like), IL-2 antagonists (e.g., tacrolimus, Fujimycin, Prograf, IL-2 fusion toxin, $DAB_{389}IL-2$, and the like), IL-4 antagonists (e.g., IL-4 fusion toxin, $DAB_{389}IL-4$, and the like), immune-mediated neuronal damage inhibitors, immunoglobins, immunostimulants (e.g., poly-ICLC, edelfosine, ET-18-OCH3, ET-18-OME, and the like), immunosuppressants (e.g., azathioprine, castanospermine, tacrolimus, FK-506, Fujimycin, Prograf, anti-leukointegrin MAb, primatized anti-CD4 antibody, linomide, roquinimex, transcyclo-pentanyl purine analogs, spanidin, 15-deoxyspergualin, deoxyspurgiline, gusperimus HCl, cyclosporine, Sandlmmune, IL-10, anti-TCR MAbs, anti-CD4 MAb, cantara, immunophilins, cyclophosphamide, and the like), integrin antagonists (e.g., anti-integrin monoclonal antibodies), interferon agonists, interferon-β1b, isoprinosine, IV methylprednisolone, macrolides, MAO B inhibitors (e.g., selegiline, Parkinyl, and the like), methotrexate, mitoxantrone, muscarinic antagonists, oxybutinin chloride, oxygen free radical antagonists (e.g., tetrandrine, biobenzylisoquinoline alkaloid, and the like), phenoxybenzamine, phospholipase C inhibitors, photodynamic therapies (e.g., benzoporphyrin derivative (BPD)), platelet activating factor antagonists (e.g., ginkgolide B), potassium channel antagonists (e.g., aminodiaquine), propranolol, prostaglandin synthase inhibitors (e.g., sulfasalazine, salazosulfa-pyridine, azulfidine, salazopyrin, and the like), protease antagonists (e.g., ginkgolide B), recombinant soluble IL-1 receptors, spergualin analogs (e.g., spanidin, 15-deoxyspergualin, deoxyspurgiline, gusperimus HCl, and the like), selectin antagonists (e.g., lectin-1, recombinant IML-1, and the like), soluble TNF receptor I, TNF antagonists (e.g., thalidomide, TNF inhibitors, and the like), and the like.

Additional treatments for which invention dithiocarbamate-containing nitric oxide scavenger(s) are advantageously employed in conjunction with the primary treating agent include administration of organ transplantation agents, such as anti-CD25 MAbs, anti-Tac antibodies, anti-TNF MAb, apoptosin, azathioprines (e.g., imuran), complement inhibiting factors (e.g., CD59), cyclosporines (e.g., CsA), FK-506/rapamycin binding proteins (FKBP), glucocorticoids, humanized version of OKT3 (e.g., huOKT3-185), hydroorotate dehydrogenase inhibitors (e.g., Brequinar), orthoclone OKT3 (e.g., IgG2a anti-T cell murine monoclonal antibody, muromonab-CD3, and the like), rapamycins, streptomyces isolates, and the like.

Additional treatments for which invention dithiocarbamate-containing nitric oxide scavenger(s) are advantageously employed in conjunction with the primary treating agent include administration of agents for the treatment of systemic lupus erythematosus (SLE), such as androgen-derived steriods, anti-CD4 humanized antibodies, CD2 antagonists, cyclosporines (e.g., Sandimmune, cyclosporine analog, cyclosporin-G, NVal-CyA, and the like), cytokines (e.g., IL-4 fusion toxin), cytokine receptor antagonists (e.g., immunomodulatory cytokines), E-selectin antagonists (e.g., anti-ELAM), FK506/tacrolimus (e.g., Prograf), hypercalcemic agents, IFN-γ antagonists (e.g., anti-IFN-γ MAb, smart anti-IFN-γ MAb, and the like), IL-1β converting enzyme inhibitors (ICE), IL-2 produced by E. coli (e.g., celmoleukin, IL-2, Celeuk, and the like), immunoglobulins (e.g., anti-ELAM), immunostimulants (e.g., thymotrinan), immunosuppressants (e.g., Rapamycin, anti-CD4, T-cell inhibitor, anti-tac MAb, immunophilins, mycophenolate mofetil, IL-4 fusion toxin, trypanosomal inhibitory factor (TIF), Leflunomide, Spanidin, 15-deoxyspergualin, deoxyspurgiline, gusperimus hydrochloride, Roquinimex, linomide, and the like), immunotoxins (e.g., Zolimomab aritox, Xomazyme-CD5 Plus, and the like), intravenous immunoglobulins, integrin antagonists (e.g., integrin blockers), Migis™ antibodies, monoclonal antibody therapeutics, murine MAb (e.g., anti-SLE vaccine, MAb 3E10, and the like), primatized anti-CD4 antibodies (e.g., CE9.1), protease inhibitors (e.g., matrix metalloprotease (MMP) inhibitors, stromelysin, and the like), protein synthesis antagonists (e.g., anti-CD6-bR, anti-T12-bR, oncolysin CD6, and the like), purine nucleoside phosphorylase inhibitors, selectin antagonists (e.g., Cylexin), spergualin analogues (e.g., Spanidin, 15-deoxyspergualin, deoxyspurgiline, gusperimus hydrochloride, and the like), T cell inhibitors (e.g., AnergiX), tumor necrosis factor (TNF) antagonists, and the like.

Additional treatments for which invention dithiocarbamate-containing nitric oxide scavenger(s) are advantageously employed in conjunction with the primary treating agent include administration of agents for the treatment of Alzheimer's disease, such as ACh release enhancers (e.g., benzothiophene derivatives), acetylcholine release stimulants, AMPA agonists (e.g., AMAlex, Isoxazole compound series, and the like), AMPA GluR agonist (e.g., IDRA-21 [7-chloro-3-methyl-3,4-dihydro-2H-1,2,4-benzothiadiazinine]), anticholinesterases, Ca-antagonists (e.g., spider venom-derived ICM peptides and analogues, substituted 2-aminoindanes compound series, and the like), K-channel blockers (e.g., Trans-R-4-(4-methoxyphenyl-methyl) cyclohexylanine and analogues, margatoxin-based functional and/or structural analogues, and the like), muscarinic receptor agonists (e.g., Xanomeline), NMDA antagonists (e.g., certain indole derivatives, $(R-(R^1,S^1))-\alpha-(4$-hydroxyphenyl)-beta-methyl-4-(phenylmenthyl)-1-piperidinepropanol and analogues thereof, and the like), nicotinic AChR agonists (e.g., ABT-418 [isoxazole, 3-meth-5-(1-meth-2-pyrrolidinyl)], and the like), and the like.

Additional treatments for which invention dithiocarbamate-containing nitric oxide scavenger(s) are advantageously employed in conjunction with the primary treating agent include administration of agents for the treatment of psoriasis, such as 5-LO inhibitors (e.g., Lonapalene, Zileuton, epocarbazolin-A, and the like), 5-LO/CO inhibitors (e.g., Tenidap), angiogenesis inhibitors (e.g., platelet factor 4), anticancer antibiotic, anti-inflammatory cytochrome P450 oxidoreductase inhibitors, antiproliferative compounds (e.g., Zyn-Linker), arachidonic acid analogues, arachidonic acid antagonists (e.g., Lonopalene, triamcinolone acetonide with penetration enhancer Azone, betamethasone dipropionate steroid wipe, Halobetasol propionate, ultravate, Halometasone, Sicorten, and the like), beta-glucan receptor antagonists, betamethasone steroid wipes, calcium metabolic moderators (e.g., Tacalcitol, Bonealfa, Calcipotriol, Dovonex, and the like), CD4 binding inhibitors, cell adhesion inhibitors (e.g., selectin inhibitor), cellular aging inhibitors (e.g., Factor X), corticosteroids (e.g., Halobetasol propionate, ultravate, Halometasone, Sicorten, and the like), dihydrofolate reductase inhibitors (e.g., dichlorobenzoprim, methotrexate, methotrexate in microsponge delivery system, and the like), E-selectin inhibitors, endogenous active form of vitarin $D_3$ (e.g., Calcitriol), fibroblast growth factor antagonists (e.g., Saporin mitotoxin, Steno-Stat, and the like), fumagillin analogues, G-proteins and signal transduction compounds, gel formulations for acne (e.g., nicotinamide, Papulex, and the like), growth hormone antagonists (e.g., Octreotide, Sandostatin, Lanreotide, angiopeptin, Somatuline, and the like), humanized antibodies (e.g., anti-CD4 antibody), hydroorotate dehydrogenase inhibitors (e.g., Brequinar sodium, bipenquinate, and the like), ICAM-1 inhibitors, IL-1 and other cytokine inhibitors (e.g., Septanil), IL-1 converting ezyme inhibitors, IL-1 receptor antagonists (e.g., Antril), IL-2 antagonists (e.g., Tacrolimus, Prograf, FK-506, and the like), IL-2 receptor-targeted fusion toxins, IL-8 receptors, immunostimulants (e.g., Thymopentin, Timunox, and the like), immunosuppressants (e.g., cyclosporine, Sandimmune, anti-CD11, Tacrolimus, Prograf, FK-506, FK-507, and the like), leukotriene antagonists, leukotriene B4 antagonists, leukotriene synthesis inhibitors, lipase clearing factor inhibitors (e.g., 1-docosanol, lidakol, and the like), lipid encapsulated reducing agent (e.g., Dithranol), liposomal gel (e.g., Dithranol), lithium succinate ointments (e.g., lithium salts, Efalith, and the like), octapeptide somatostatin analogues (e.g., Lanreotide, angiopeptin, Somatuline, and the like), PKC inhibitors, phospholipase A2 compounds, photodynamic anticancer agents (e.g., 5-aminolevulinic acid), photodynamic therapies (e.g., benzoporphyrin derivatives, synthetic chlorins, synthetic porphyrins, and the like), PKC inhibitors (e.g., Safingol, Kynac, and the like), platelet activating factor antagonists, platelet aggregation inhibitors (e.g., CPC-A), prostaglandin agonists (e.g., eicosapentaenoic acid+gamma-linolenic acid combination, Efamol Marine, and the like), protein kinase C (PKC) inhibitors, protein synthesis antagonists (e.g., Calcitriol, Namirotene, and the like), purine nucleoside phosphorylase inhibitors, radical formation agonists (e.g., benzoporphyrin derivatives), recombinant antileukoproteinases, retinoids, retinoid derivatives, rapamycin binding proteins (FKBP) (e.g., immunophilins), second generation monoaromatic retinoids (e.g., Acitretin, Neotigason, and the like), soluble IL-1, IL-4 and IL-7 receptors, somatostatin analogues (e.g., Octreotide, Sandostatin, and the like), superoxide dismutase, thymidylate synthase inhibitors, transglutaminase inhibitors, tyrphostin EGF receptor kinase blockers, VCAM-1 inhibitors, and the like.

Still further treatments for which invention dithiocarbamate-containing nitric oxide scavenger(s) are advantageously employed in conjunction with the primary treating agent include administration of agents for the treatment of diabetes, such as ACE inhibitors (e.g., captopril), amylin agonists and antagonists (e.g., Normylin™), autoimmune compounds, capsaicins (e.g., Zostrix-HP), domperidones (e.g., Motilium®), fluvastatins (e.g., Lescol), iloprost, insulin analogs (e.g., Nu-Insulin compounds, Humulin, Iletin, Humalog™, LYs-Pro, Amaryl, and the like), insulin-like growth factors, insulinotropins, nerve growth factors, oral hypoglycernics (e.g., glimepiride, Amaryl, acarbose, miglitol, recombinant yeast glucagon, GlucaGen™, NovoNorm™, glipizide, insulinotropin, and the like), platelet-derived growth factors (e.g., ZymoGenetics/NovoNordisk compounds), sulfonylureas (e.g., tolbutamide, acetohexarnide, tolazamide, chlorpropramide, and the like), T cell approaches (e.g., anergize, Procept compounds, T cell Sciences compounds, and the like), tolrestats (e.g., Alredase®, and the like), and the like.

Additional treatments for which invention dithiocarbamate-containing nitric oxide scavenger(s) are advantageously employed in conjunction with the primary treating agent include the administration of agents for the treatment of stroke, such as Ancrod, 5-HT antagonists (e.g., Piperazine derivatives), 5-HT reuptake inhibitors (e.g., Milnacipran, Dalcipran, and the like), 5-HT agonists, 5-lipoxygenase inhibitors, ACH agonists (e.g., Pramiracetam, Choline-L-alfoscerate, L-alpha-glycerylphosphoryl-choline, Delecit, and the like), adenosine agonists (e.g., arasine analogs), adenosine A1 receptor agonists (e.g., Azaisotere, 2-chloro-N-[4 (phenylthio)-1-piperidinyl] adenosine, and the like), adenosine reuptake inhibitors (e.g., Diphenyloxazole derivatives), adrenergic transmitter re-uptake inhibitors (e.g., Bifemelane, Alnert, Celeport, and the like), aldose reductase inhibitors (e.g., Spiro-3' pyrroline derivatives), alpha antagonists (e.g., Drotaverine acephyllinate, Depogen, and the like), alpha 2 agonists, Ancrod/Arvin, aspirin, benzothiazoles (e.g., Lubeluzole, and the like), benzodiazepine receptor antagonists (e.g., 3-oxadiazolyl-1,6-naphthyridine derivatives, Tetracyclic imidazodiazepineseries imidazenil, and the like), blood substitutes, bradykinin antagonists (e.g., Bradycor, Septicor, and the like), C5a release inhibitors (e.g., protein derivative), calcium antagonists (e.g., Lemildipine, Trimetazidine derivatives, lomerizine, Diltiazem analog clentiazem maleate, and the like), calcium channel antagonists (e.g., nitrendipine-like compound diperdipine, Diltiazem derivative, tetrahydronaphthalene derivatives, fasudil, Eril, darodipine, dazodipine, Dihydropyridine, Lacidipine, Nilvadipine, and the like), calpain inhibitors, carnitine palmitoyl-transferase inhibitors, carvedilol, cell adhesion molecular technology, cerebral calcium antagonist vasodilators (e.g., Nimodipine, Nimotop, and the like), cholinesterase inhibitors (e.g., indole and indazole derivatives, Tacrine analogs, and the like), complement factor inhibitors (e.g., protein derivative TP16, compinact A, compinact C, Factor D inhibitors, soluble, recombinant MCP-based complement inhibitors, and the like), complement inhibitors, coronary vasodilators (e.g., Nicorandil, Adancor, and the like), cytidyl diphosphocholine/citicholines, cytokines, Dexanabiol, dopamine agonists, endothelin antagonists, endothelin receptor antagonists, excitatory amino acid agonists (e.g., acylated polyamine analogs, N-(4-hydroxyphenylpropa-noyl)-spermine analogs, and the like), excitatory amino acid antagonists (e.g., Tryptophan, 4,6-disubstituted stroke and kynurenine derivatives, and the like), glutamate antagonists (e.g., Kainate, quisqualate, and the like), glutamate receptor antagonists (e.g., Araxin compounds, Quinoxaline derivative, and the like), glycine antagonists, glycine NMDA agonists (e.g., 3-hydroxy-2,5-dioxo-1H-benz[b]azepines), glycine NMDA associated antagonists (e.g., Strychnine-insensitive glycine binding site of NMDA receptor, Glystasins, eliprodil, and the like), growth factor antagonists (e.g., non-peptide indolocarbazole neutrophic molecules, and the like), GPIIb/IIIa antagonists, heparin, hydroxyl radical formation inhibitors (e.g., homopiperazine derivatives), hypocalcemic agents (e.g., calcitonin peptide, related to hCGRP peptide), ICAM-1 compounds (e.g., Enlimomab), Interleukin-1 antagonists (e.g., cyclic nitrones), iron-dependent lipid peroxidation inhibitors (e.g., 2-(amino-methyl) chromans), lactic acid accumulation/inhibitors, lipid peroxidase inhibitors (e.g., Idebenone, Avan, and the like), methyltransferase stimulants (e.g., 4-methyl benzenesulfonate, ademetionine sulfate tosilate, Ceritan, and the like), monoamine oxidase B inhibitors (e.g., Lazabemide), nadroparin (e.g., Fraxiparin), nafronyl/naftidrofuryl (e.g., Praxilene), nerve growth factor agonists (e.g., small molecule compounds, monosialoganglioside GM1, and the like), neuronal calcium channel blockers, NMDA antagonists (e.g., Spiroisoindoles/dizocilpine derivatives, Oxindole compound, Sialic acid derivative, N-palmitoyl-Betaethylglycoside neuraminic acid, Dextrorphan, Ifenprodil analogue eliprodil, Lipophilic molecules, Remacemide, and the like), NMDA antagonist-partial agonists (e.g., Conantokin G peptide), NMDA channel blockers (e.g., Aptiganel, CERESTAT, and the like), NMDA receptor antagonists, nootropic/acetylcholine agonists (e.g., Oxiracetam, Neuractiv, and the like), norepinephrine inhibitors (e.g., Midalcipran), N-type calcium channel antagonists, opioid antagonists (e.g., Nalmefene, nalmetrene, Cervene, Incystene, and the like), opioid kappa receptor agonists (e.g., acrylacetamide enadoline), organoselenims (e.g., Ebselen), oxygen scavengers (e.g., Tirilazad mesylate, Lazaroids, Freedox, and the like), PAF antagonists (e.g., nupafant), partial glycine NMDA agonists (e.g., ACPC), peptide/GPIIb/IIIa antagonists (e.g., Integrelin), peptidic neuron-specific calcium channel antagonists, phosphodiesterase inhibitors (e.g., Xanthine derivatives, propentofylline, Hoe-285, Hextol, and the like), plasminogen activators (e.g., r-ProUK (recombinant pro-urokinase), platelet-activating factor antagonists, platelet aggregation antagonists (e.g., cilostazol, peptide agents, GPIIb-IIIA inhibitor, and the like), platelet aggregation Inhibitors (e.g., Diarninoalkanloic acid derivatives), potassium channel agonists (e.g., Nicorandil, Adancor, and the like), prolyl endopeptidase (PEP) inhibitors, protein kinase C inhibitors (e.g., monosialoganglioside derivatives), proteolytic enzyme inhibitors (e.g., Protease nexin-1, Incyte, Nafamostat, Duthan, Futhan, and the like), pyrimidine derivatives, Quinolizine derivatives, recombinant tissue plasminogen activators (e.g., alteplase, Activase, and the like), Schwann cell derived molecules/promoters, sigma receptor antagonists (e.g., tetrahyropyridinyl-isoxazolines), sodium/calcium channel modulators (e.g., Lifarizine), sodium channel antagonists, streptokinase (e.g., Streptase), superoxide dismutase stimulants (e.g., PEG conjugated enzyme superoxide dismutase/Dismutec, PEG-SOD, and the like), thrombin inhibitors, (e.g., non-peptide), thromboxane synthase inhibitors (e.g., Linotroban), thyrotropin-releasing hormone agonists (e.g., TRH agonists, Protirelin analogthymoliberin, and the like), ticlopidine (e.g., Ticlid), TRH agonists (e.g., Thyrotropin releasing hormones), trilazard, urokinase (e.g., Abbokinase), warfarin (e.g., Coumadin), and the like.

Accordingly, presently preferred indications for treatment in accordance with the combinational therapy aspect of the present invention include septic shock, ischemia, ulcers, ulcerative colitis, diabetes, arthritis, asthma, Alzheimer's disease, Parlnnson's disease, multiple sclerosis, cirrhosis or allograft rejection, and the like.

In accordance with a particular aspect of the present invention, the dithiocarbamate-containing nitric oxide scavenging agent is administered in combination with one or more of the above-described agents, optionally including an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmaceutical agents and/or the indications they are designed to address (e.g., systemic hypotension) can be prevented or reduced by co-administration of a combination reagent including a dithiocarbamate-containing nitric oxide scavenger.

Those of skill in the art recognize that the combination of an agent capable of inactivating species which induce the expression of inducible nitric oxide (or an agent capable of inhibiting the production of such species), and dithiocarbamate-containing nitric oxide scavengers described herein can be delivered in a variety of ways, such as, for example, orally, topically, intravenously, subcutaneously, parenterally, rectally, by inhalation, and the like.

Since individual subjects may present a wide variation in severity of symptoms and each drug has its unique therapeutic characteristics, the precise mode of administration, dosage employed and treatment protocol for each subject is left to the discretion of the practitioner.

In accordance with still another embodiment of the present invention, there are provided physiologically active composition(s) comprising a "therapeutic agent" (as described herein) and a dithiocarbamate-containing nitric oxide scavenging compound, as described herein, in a suitable vehicle rendering said composition amenable to oral delivery, transdermal delivery, intravenous delivery, intramuscular delivery, topical delivery, nasal delivery, and the like.

Depending on the mode of delivery employed, the above-described compositions can be delivered in a variety of pharmaceutically acceptable forms. For example, the above-described compositions can be delivered in the form of a solid, solution, emulsion, dispersion, micelle, liposome, and the like.

The invention will now be described in greater detail by reference to the following non-limiting examples.

EXAMPLE 1

Preparation of Poly MGD-BSA by Crosslinking

The crosslinking experiments were performed as follows: One ml of bovine serum albumin (BSA; 0.1 to 2.0 mM in water) was added to a 10-ml beaker containing an aliquot of 20-400 mM N-hydroxysulfosuccinimidyl-4-azido salicylic acid (Sulfo-NHS-ASA; Piece Chemical Co) in DMSO, at pH 7.0. The reaction mixture was incubated at ambient temperature for 10–60 min with slow stirring in the dark. Upon the addition of N-methyl-D-glucamine dithiocarbamate (MGD; 5 to 100 mg), the solution was irradiated at 365 nm using an UV lamp for 1–5 min. After irradiation, the solution was applied to a G-25 pre-packed column. The MGD-BSA containing fractions were collected and rechromatographed once. The stoichiometry of MGD bound to the BSA molecule can be estimated by measuring the absorbance at 215 nm (for MGD) and 280 nm (for BSA).

EXAMPLE 2

Preparation of Poly MGD-BSA by Nonspecific Binding

Serum albumin is known to be a carrier for fatty acids, amino acids and drugs (see, Halliwell, supra). The procedure for the preparation of nonspecific binding of MGD to BSA is as follows: One ml of bovine serum albumin (BSA; 0.1 to 2.0 mM in water, pH 7.0) was added to a 10-ml beaker and the solution was gently stirred until completely dissolved. MGD (5 to 100 mg) was added to the above solution and incubated at ambient temperature for 5 to 60 min. The solution was applied to a G-25 pre-packed column. The stoichiometry of MGD bound to the BSA molecule can be estimated spectroscopically as described above.

EXAMPLE 3

Preparation of Poly [(MGD)$_2$-Fe]-BSA

The procedures for the preparations of the MGD-crosslinked BSA complex and the MGD nonspecific bound to BSA were the same as described in Examples 1 and 2, respectively. Ferrous sulfate (2–20 mg) was added to the purified MGD-BSA complexes prior to column separation. The protein fractions turned dark brown color, indicative of the presence of the [(MGD)$_2$-Fe] complexes.

EXAMPLE 4

Focal Cerebral Ischemia-Reperfusion Model in Rats

Long-Evans rats (325±25 g) were anesthetized with isoflurane and the right middle cerebral artery (RCA) was exposed and occluded as described previously (see, for example, He et. al., in Am. J. Physiol. 265:H252–256 (1993)). Both carotid arteries were occluded with atraumatic aneurysm clips. After 45 minutes of ischemia, reperfusion was initiated in all occluded vessels. Core temperature (determined by rectal probe) and temporalis muscle temperature were maintained at 37±0.5° C. using heat lamps. Arterial blood samples were collected at various intervals for determination of blood gas and plasma glucose content before, during and after ischemia.

EXAMPLE 5

Neuroprotective Effects of N-Methyl-D-Glucamine Dithiocarbamate (MGD) in the Rat Ischemic Stroke Model After one to four hours of reperfusion, the rats were infused intravenously with either 2 ml of an MGD/BSA solution in saline (containing 24 mg of MGD and 50 mg of bovine serum albumin (BSA)) or 2 ml of a BSA solution (containing 50 mg of BSA in saline) at an infusion rate of 2 ml/hr for one hour. The animals were sacrificed 24 hours after the initiation of ischemia, and brain edema was quantified as previously described (see, for example, Lin et al., in Stroke 24:117–121 (1993)). The remaining animals were also sacrificed 24 hours after initiation of ischemia, and brain infarct volumes were then quantified by sectioning and staining with 2,3,5-riphenyltetrazolium chloride (TTC) in saline, and visualization of the infarct volume using an image analysis system as described by Lin et al., supra.

The results presented in FIG. 1 show that treatment with MGD+BSA, compared to treatment with vehicle alone (BSA), results in about 40% reduction in infarct volume (p<0.0215).

While the invention has been described in detail with reference to certain preferred embodiments thereof, it will be understood that modifications and variations are within the spirit and scope of that which is described and claimed.

That which is claimed is:

1. A therapeutic complex comprising a dithiocarbamate non-covalently associated with a macromolecule, wherein said complex is further complexed with iron, and wherein the dithiocarbamate and the macromolecule are combined at a pH of about 7.

2. The complex according to claim 1 wherein said macromolecule is a polynucleic acid.

3. The complex according to claim 1 wherein said macromolecule is a polysaccharide.

4. The complex according to claim 3 wherein said polysaccharide is selected from the group consisting of dextran, hyaluronic acid, cellulose, starch, and glycogen.

5. The complex according to claim 1 wherein said macromolecule is a polypeptide.

6. The derivative according to claim 5 wherein said polypeptide is a synthetic protein.

7. The derivative according to claim 5 wherein said polypeptide is a naturally occurring protein.

8. The complex according to claim 7 wherein said protein is serum albumin.

9. The derivative according to claim 5 wherein said polypeptide is a modified naturally occurring protein.

10. The complex according to claim 1 wherein said dithiocarbamate is selected from compounds having to structure:

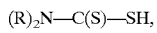

$(R)_2N—C(S)—SH$, wherein:
each R is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, or to two R groups can cooperate to form a 5-, 6- or 7-membered ring including N and the two R groups, or either of the R groups is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis (dithiocarbamate) species.

11. The complex according to claim 10 wherein said macromolecule is a polysaccharide.

12. The complex according to claim 11 wherein said polysaccharide is selected from the group consisting of dextran, hyaluronic acid, cellulose, starch, and glycogen.

13. The derivative according to claim 10 wherein said macromolecule is a polynucleic acid.

14. The complex according to claim 10 wherein said macromolecule is a polypeptide.

15. The derivative according to claim 14 wherein said polypeptide is a synthetic protein.

16. The derivative according to claim 14 wherein said polypeptide is a naturally occurring protein.

17. The complex according claim 16 wherein said protein is serum albumin.

18. The complex according to claim 14 wherein said polypeptide is a modified naturally occurring protein.

* * * * *

UNITED STATES PATENT AND TRADEMARK OFFICE
CERTIFICATE OF CORRECTION

PATENT NO. : 6,649,591 B2
DATED : November 18, 2003
INVENTOR(S) : Ching-San Lai

It is certified that error appears in the above-identified patent and that said Letters Patent is hereby corrected as shown below:

<u>Title page, Item [54] and Column 1, lines 1 and 2,</u>
Title, change "POLYDITHICARBAMATE" to -- POLYDITHIOCARBAMATE --; and change "MARCOMOLECULES" to -- MACROMOLECULES --

<u>Column 28,</u>
Line 21, after the word "having," change "to" to -- the --
Line 36, before the word "two," change "to" to -- the --

Signed and Sealed this

Twenty-seventh Day of April, 2004

JON W. DUDAS
*Acting Director of the United States Patent and Trademark Office*